United States Patent
Levitsky et al.

(12) 
(10) Patent No.: US 6,623,973 B2
(45) Date of Patent: Sep. 23, 2003

(54) METHOD FOR DETECTION OF ORGANIC VAPORS BASED ON FLUORESCENCE ENHANCEMENT IN PORPHYRIN AGGREGATES

(75) Inventors: Igor A. Levitsky, Fall River, MA (US); Sergei G. Krivoshlykov, Shrewsbury, MA (US)

(73) Assignee: Altair Center, LLC., Shrewsbury, MA (US)

( * ) Notice: Subject to any disclaimer, the term of this patent is extended or adjusted under 35 U.S.C. 154(b) by 275 days.

(21) Appl. No.: 09/826,257

(22) Filed: Apr. 4, 2001

(65) Prior Publication Data

US 2002/0146837 A1 Oct. 10, 2002

(51) Int. Cl.[7] .................. G01N 33/00; G01N 21/00; G01N 21/75; G01N 21/76
(52) U.S. Cl. .................. 436/104; 436/164; 436/166; 436/167; 436/172
(58) Field of Search ................ 436/164, 166, 436/167, 172, 104; 422/82.05–82.09, 82.11

(56) References Cited

U.S. PATENT DOCUMENTS 5,744,302 A * 4/1998 Sessler et al. .................. 435/6

OTHER PUBLICATIONS

Purrello et al. "porphyrin Assemblies as Chemical Sensors", Coordination Chemistry Reviews, 1999, 190–192, pp. 683–706.*

Nakamura et al. "Highly Sensitive Spectrofluorometric Determination of Nucleic Acid based on the Aggregatin of Two Oppositely Charged Kinds of WQater–Soluble Porphyrynes", Anal. Letters, 1996, 29 (14), pp. 2453–2461.*

Amao et al. "Oxygen Sensing Using Palladium Porphyrin With Long Alkyl Chain Self–Assembled Film", Journal of Porphyrins and Phthalocyanines (2000), 4(1), 19–22 (Abstract).*

Li et al. "Porphyrin Based Self–Assembled Monolayer Thin Films: Synthesis and Characterization", J. Am. Chem. Soc., 1993, 115 (15) 6975–80.*

* cited by examiner

*Primary Examiner*—Jill Warden
*Assistant Examiner*—Yelena Gakh (57) ABSTRACT

A fluorescence-based method for highly sensitive and selective detection of volatile organic compounds such as vapors of benzene, alcohol, chloroform, dimethyl methylphosphonate (DMMP) that is a simulant of Sarin, Soman and other chemical warfare agents, is proposed. The method employs the effect of strong fluorescence change in thin films of aggregated porphyrins. In one preferred embodiment, the aggregation of porphyrin molecules leads to initial depression of chromophore emission due to self-quenching effect. The binding of analyte molecules to porphyrin sensitive layer forms porphyrin-analyte complexes, which destroy initial aggregate structure and induce the strong fluorescence enhancement. Aggregate-sensing films usually provide higher and faster response than porphyrins isolated in a polymer matrix. That results in strong enhancement of the florescence quantum yield and shift of the fluorescent spectrum in the direction of shorter wavelengths. The method can be used in fluorescence chemical sensors of organic vapors for different applications including environmental monitoring, control of industrial processes and medicine.

8 Claims, 8 Drawing Sheets

PSFA

PMMA

METHOD FOR DETECTION OF ORGANIC VAPORS BASED ON FLUORESCENCE ENHANCEMENT IN PORPHYRIN AGGREGATES

This invention was made with Government support under Grant N00014-00-M-0140 awarded by the BMDO. The Government has certain rights in this invention.

BACKGROUND OF THE INVENTION

1. Field of the Invention

The present invention relates to the methods for detection of vapors, and particularly to the fluorescence-based method of detection employing solid films of sensory porphyrins in the aggregated form. In one preferred embodiment, the aggregation of porphyrin molecules leads to initial depression of chromophore emission due to self-quenching effect. The binding of analyte molecules to porphyrin sensitive layer forms porphyrin-analyte complexes, which destroy initial aggregate structure and induce the strong fluorescence enhancement. Aggregate-sensing films usually provide higher and faster response than porphyrins isolated in a polymer matrix. Such effect is new and its application can considerably improve the sensor performance. In another preferred embodiment, the sensitive material is incorporated into an optical fiber system enabling efficient excitation of the dye and collecting the fluorescent signal form the sensitive material on the remote end of the system.

The method can be used in all applications where highly sensitive detection of volatile organic compounds, such as vapors of benzene, alcohol, chloroform, dimethyl methylphosphonate (DMMP) that is a simulant of Sarin, Soman and other chemical warfare agents, is required for environmental monitoring, chemical industry and medicine.

2. Background of the Invention

Today, there is a high demand for chemical sensor for detecting low concentration levels of analytes present in the liquid and gaseous phase. Selectivity to target molecules is also highly desired. Traditional methods of quantitative detection of analytes based on gas chromatography and mass spectrometry require complex laboratory equipment. Among modern approaches for real time monitoring of gaseous analytes, mainly three kinds of sensing elements have been investigated: microelectrodes, quartz crystal microbalance and surface acoustic wave devices. Generally all these methods are based on detection of only one parameter—signal intensity. Therefore reliable analyte identification requires significant increasing the number of individual sensors in the detector array.

Meanwhile, optical chemosensors, especially fluorescence-based chemosensors can provide many kinds of complex information, including changes in intensity, wavelengths and spectral shape, fluorescence lifetime. Hence such promising approach allowing detection of many parameters simultaneously should make possible the fabrication of highly sensitive, robust, multi-analyte-detecting arrays with fewer independent sensors. Moreover, the possibility of remote sensing using optical fluorescence technique offers many serious advantages over other traditional methods of real-time monitoring of toxic gases and pollutants.

Usually for luminescence sensing the porphyrins are immobilized in the neutral polymer films, sol-gel matrixes or membranes. The main idea of the matrix isolation is the prevention of porphyrin aggregation leading to the strong fluorescence selfquenching. Nothing has been reported yet about the design of fluorescence chemosensors based on thin films of aggregated porphyrins employing the fluorescence enhancement under gas exposure.

The present invention suggests new approach to the highly sensitive and selective detection of organic vapors using fluorescence properties of aggregated porphyrins. It is based on recently demonstrated new effect of strong enhancement of the fluorescence emission in the presence of molecules of organic vapors. In one preferred embodiment the fluorescent sensitive material is incorporated into a fiber-optical system allowing remote monitoring of large contaminated area.

The method can be used in all applications where highly sensitive detection of volatile organic compounds, such as vapors of benzene, alcohol, chloroform, dimethyl methylphosphonate (DMMP) that is a simulant of Sarin, Soman and other chemical warfare agents, is required for environmental monitoring, chemical industry and medicine.

OBJECTS AND SUMMARY OF THE INVENTION

It is an object of the present invention to improve performance of chemical sensors of organic vapors by employing the effect of fluorescence change of the thin films of aggregated porphyrins in the presence of target molecules.

Another object of the invention is to provide a simple and efficient method of detection of the fluorescence signal by measuring enhancement of the fluorescence in the presence of target vapors.

A further object is to provide a selection of efficient sensitive fluorescent material comprising a film of Tetraphenylporphyrin (TPP) and metaloporphyrin Zn-Tetraphenylporphyrin (Zn-TPP) aggregates.

Another object is to provide efficient method of processing the fluorescent signal from the sensitive material.

Still another object is to provide a possibility of remote monitoring of large contaminated area by incorporating the sensitive fluorescent material into an optical fiber system.

An additional object of the invention is to provide a method for fabrication of the fiber-optic fluorescence sensors achieving efficient excitation of the sensitive material and efficient collecting the fluorescence signal.

Briefly stated, the present invention provides a method of detection of different volatile organic compounds such as, vapors of benzene, alcohol, chloroform, dimethyl methylphosphonate (DMMP) that is a simulant of Sarin, Soman and other chemical warfare agents. The method employs the effect of strong fluorescence change in the thin films of aggregated porphyrins in the presence of target vapors.

The aggregation of porphyrin molecules leads to initial depression of chromophore emission due to self-quenching effect. The binding of analyte molecules to porphyrin sensitive layer forms porphyrin-analyte complexes, which destroy initial aggregate structure. That results in strong enhancement of the dye florescence quantum yield, appearance of new bands and shift of the dye fluorescent spectrum in the direction of shorter wavelengths. The method can be used in fluorescence chemical sensors of organic vapors for different applications including environmental monitoring, control of industrial processes and medicine.

The above, and other objects, features and advantages of the present invitation will become apparent from the following description read in conjunction with the accompanying drawings.

DESCRIPTION OF PREFERRED EMBODIMENTS

The invention provides a new method for detection of organic vapors employing fluorescence of thin films of aggregated porphyrins. The aggregated form of porphyrins are chosen such to maximize the influence of the organic vapors under detection on the fluorescence light signal from the sensitive material. The proposed general method of detection of basic vapors can be used for the design of many different chemical sensors and fluorescence-based devices.

Figure 1:
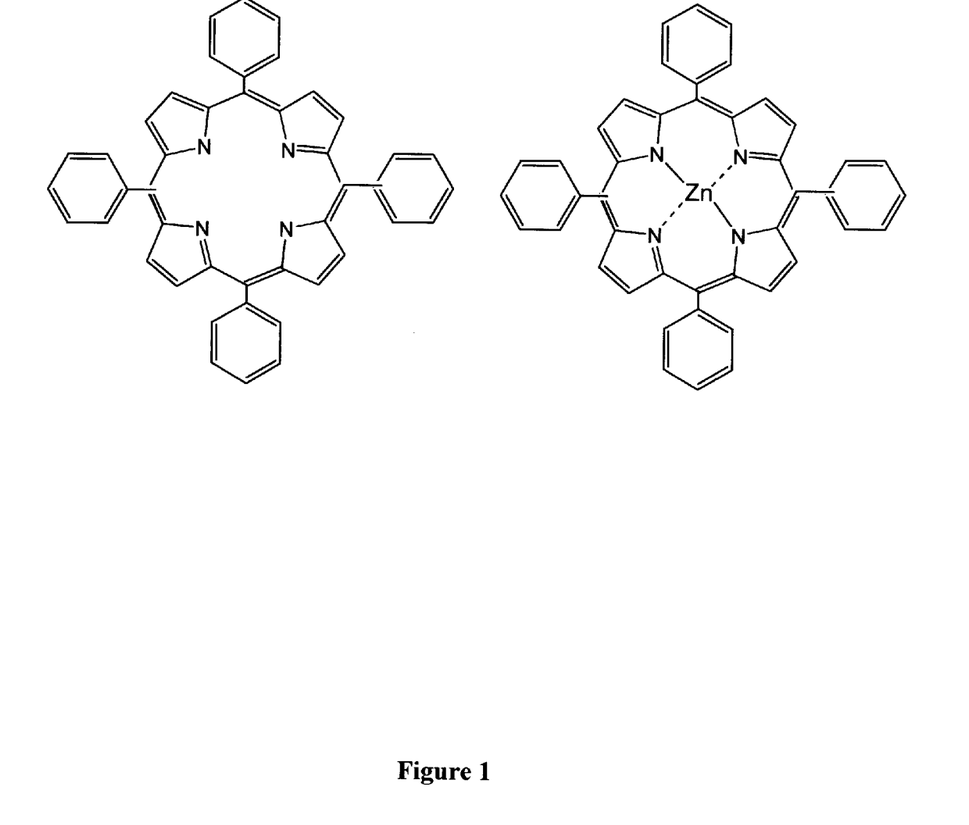
FIG. 1 shows the structure of TPP and Zn-TPP.
Figure 2:
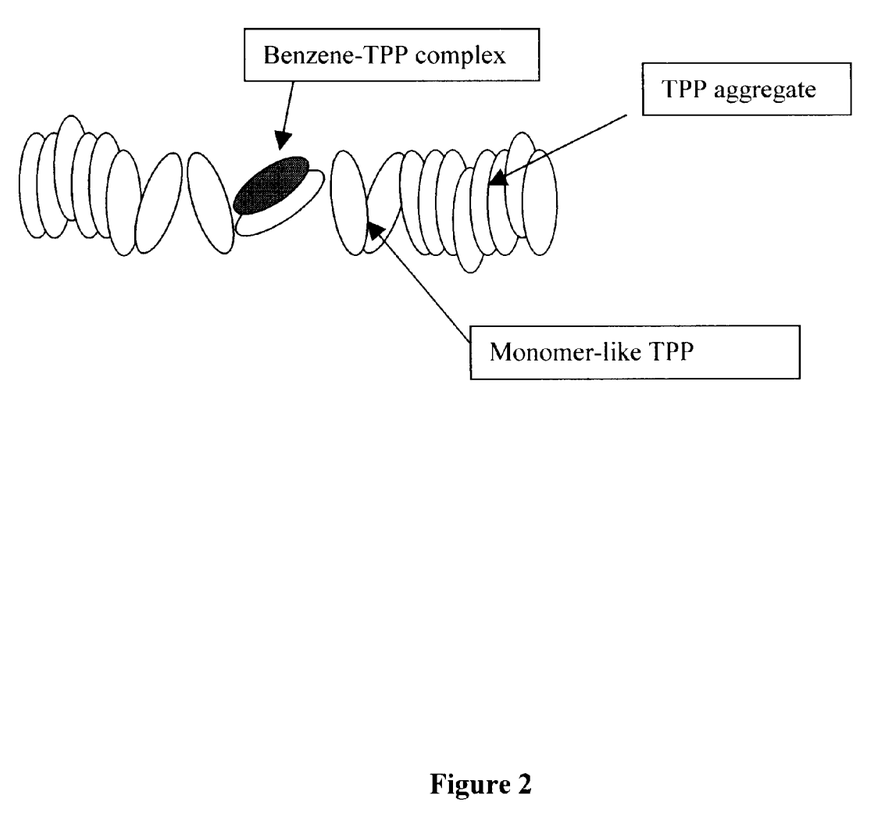
FIG. 2 illustrates benzene-TPP complex formation in TPP aggregates.
Figure 3:
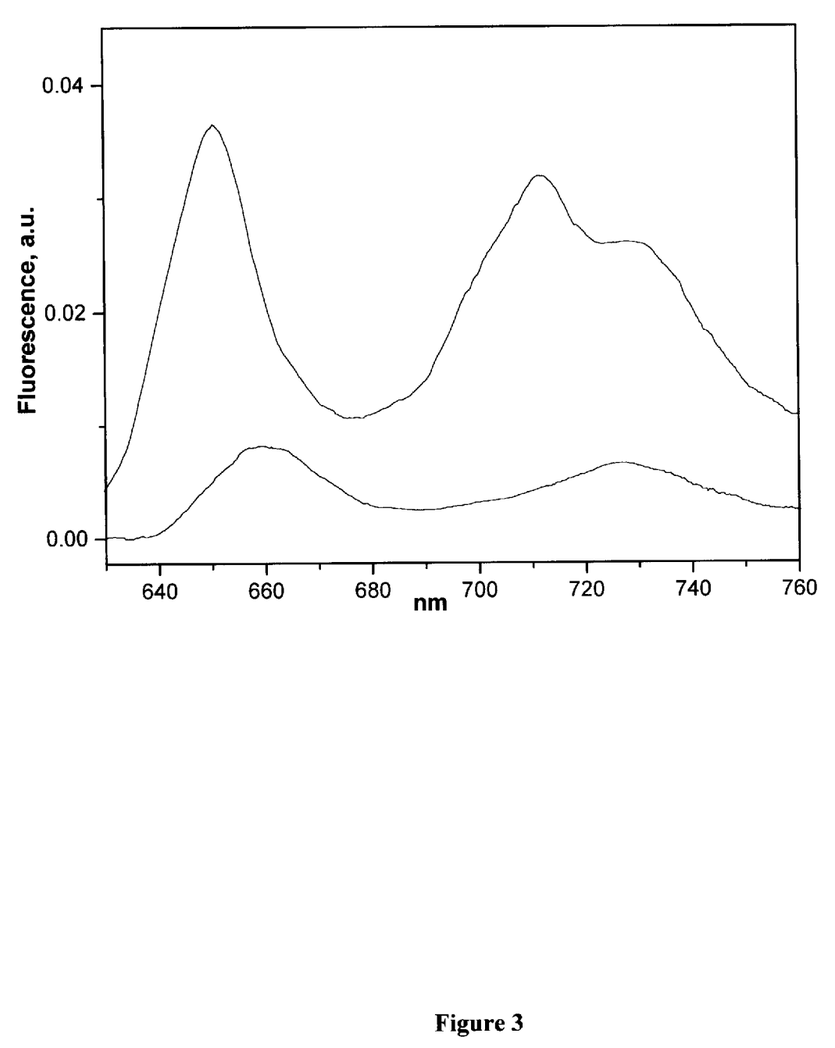
FIG. 3 demonstrates TPP aggregate fluorescence prior (dotted line, bottom) and after 10 min (solid line, top) of benzene exposure.
Figure 4:
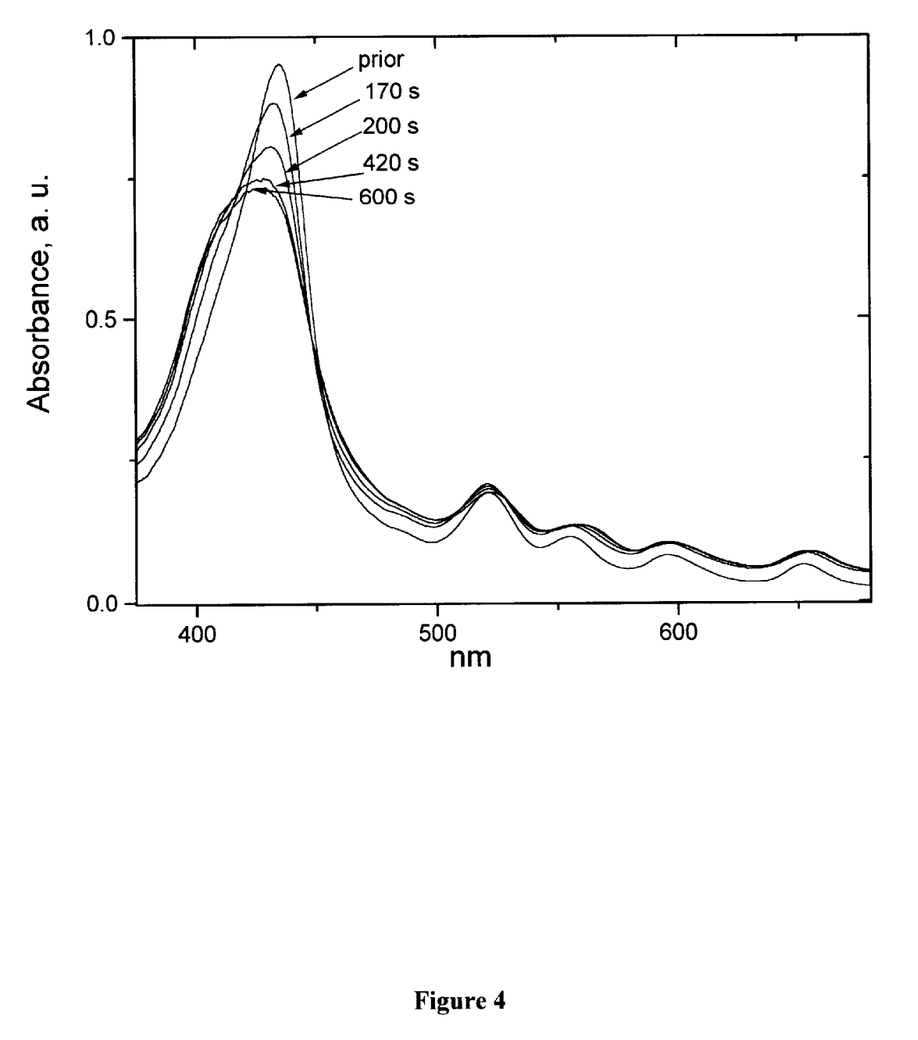
FIG. 4 shows evolution of absorption spectrum of TPP aggregate film under benzene exposure.
Figure 5:
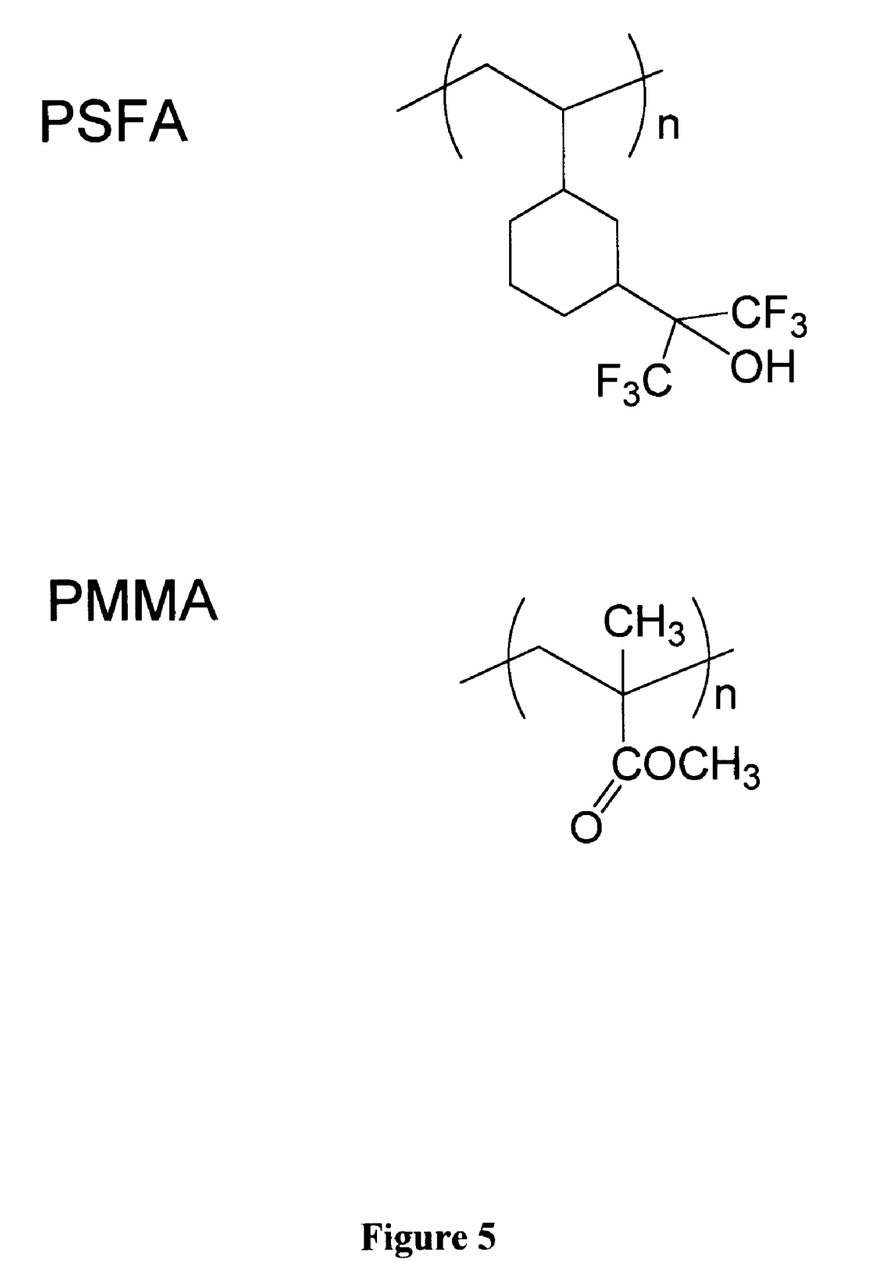
FIG. 5 shows the structure of PSFA and PMMA polymers.

In one preferred embodiment the aggregated TPP and Zn-TPP molecules (FIG. 1) are chosen such that the interaction between molecules forming the aggregates results in depression of the fluorescence yield of the sensitive material prior to its interaction with the vapors. Then interaction between the vapors of benzene and aggregated porphyrins breaks the porphyrin aggregated stack "releasing" the dye and returning it back into monomer-like state (FIG. 2). That results in strong enhancement of the dye florescence quantum yield and appearance of a new spectral band corresponding to monomer-like TPP molecules (FIG. 3). The absorption spectrum of TPP aggregates demonstrates also the strong change (FIG. 4). The isobestic point (FIG. 4) indicates to coexisting of two species: new monomer-like TPP molecules and former aggregates. No sizable change of the absorption was observed in the films of TPP molecules isolated in PMMA and PSFA polymer matrix. PMMA and PSFA (strong hydrogen-bond acidic properties) were employed as isolated matrixes for TPP and Zn-TPP to compare their fluorescence response with aggregated TPP and Zn-TPP. The structure of the PMMA and PSFA polymers is shown in FIG. 5.

In the preferred embodiment an additional source of the strong fluorescence enhancement in TPP aggregate can be the energy transfer/migration leading to antenna effect. In this case electronic excitations migrate from remote aggregate regions to the benzen-TPP complex and monomer-like TPP molecules and are captured by them. Hence the fluorescence from these sites should be amplified as a result of the light harvesting process.

Figure 6:
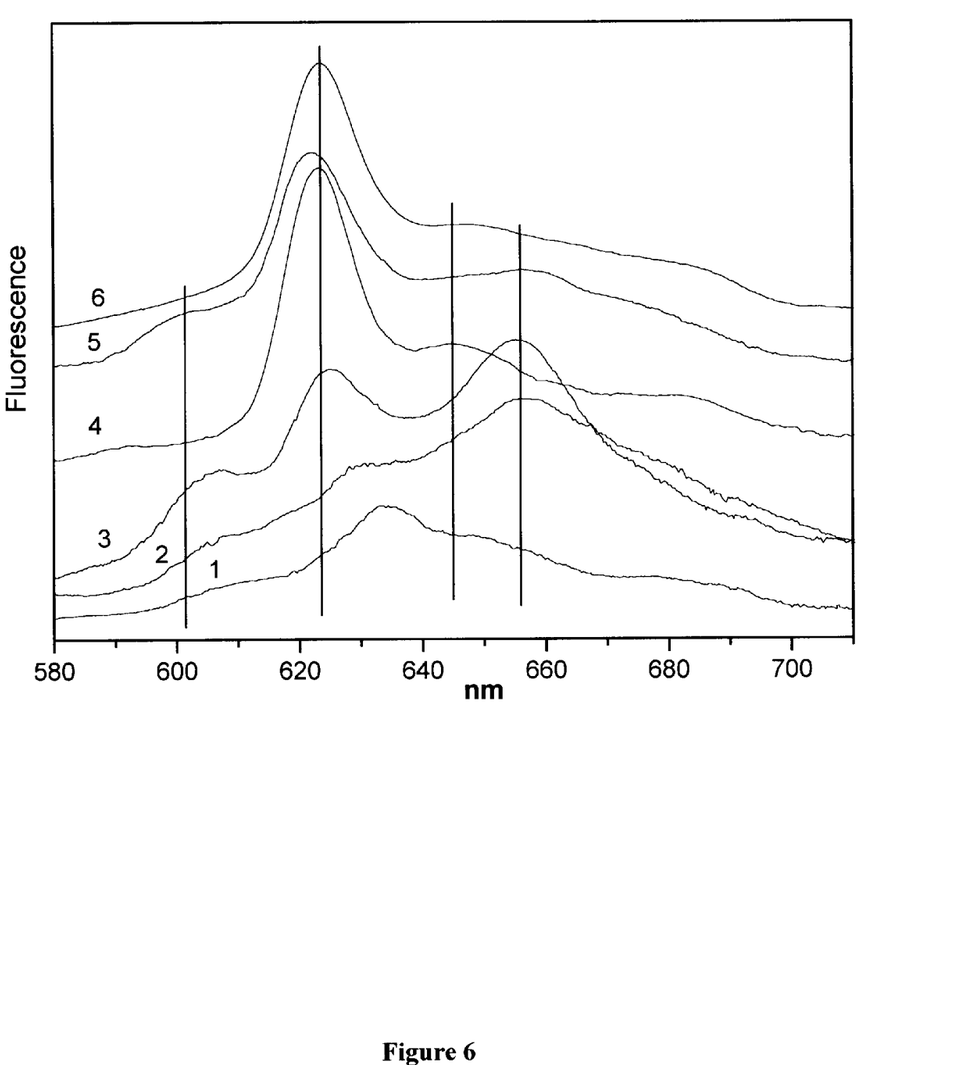
FIG. 6 demonstrates Zn-TPP fluorescence after 10 min exposure under vapors: 1—prior exposure, 2—DIAM, 3—DMMP, 4—chloroform, 5—ethyl alcohol, 6—benzene.

In another preferred embodiment the significant difference between Zn-TPP and TPP molecules related to their receptor properties is the ability of Zn-TPP to coordinate the axial ligand and form metalocomplexes with various organic molecules. Another feature that was found is a rich spectral structure of the Zn-TPP aggregate fluorescence as distinct from matrix-isolated films. Fluorescence spectrum of Zn-TPP aggregate comprises four spectral bands. Meanwhile that of matrix-isolated chromophore displays only two bands without any appreciable change (spectral shift and redistribution of intensities) under the analyte exposure. FIG. 6 shows considerably different Zn-TPP fluorescence spectra of aggregate films after 10 minutes of exposure under five analyte vapors. Here the formation of analyte-Zn-TPP complex is more complicated process than for TPP aggregates. Complete understanding of spectral evolution under analyte exposure needs an additional study involving time-resolved spectroscopy, excitation spectra and theoretical calculations and modeling.

For sensing approach the diversity of the spectral shape gives a unique possibility to identify each analyte vapors according to its fluorescence spectrum. For example, benzene, EtOH and chloroform exposed spectra have the strongest band at 623 nm, however spectrum after EtOH exposure displays sizable short-wavelength band at 602 nm as distinct from chloroform and benzene. Further, benzene exposed spectrum can be separated from chloroform one by comparison between long wavelength bands at 645 nm and 685 nm. DMMP and diethylamine (DIAM) exposed spectra considerably differ from others, probably, as a result of the analyte basic properties. For these spectra the dominant band is located at 656 nm. However, comparison of these spectra clearly indicates which analyte vapor (DMMP or DIAM) was applied. Thus, the spectral modification of Zn-TPP aggregate films provides a specific "fingerprint" for each analyte vapor. This effect can be successfully applied for multi-wavelength sensing that should significantly increase the sensor selectivity and discriminate the false response from possible interferants. One example of multi-wavelength sensing for Zn-TPP aggregates is detection of signal ratio A/B, A/C, A/D, B/C, B/D, C/D for fluorescence intensity A, B, C, D at 602 nm, 623 nm, 645 nm, 656 nm (depicted in FIG. 6 as dash vertical lines).

Figure 7:
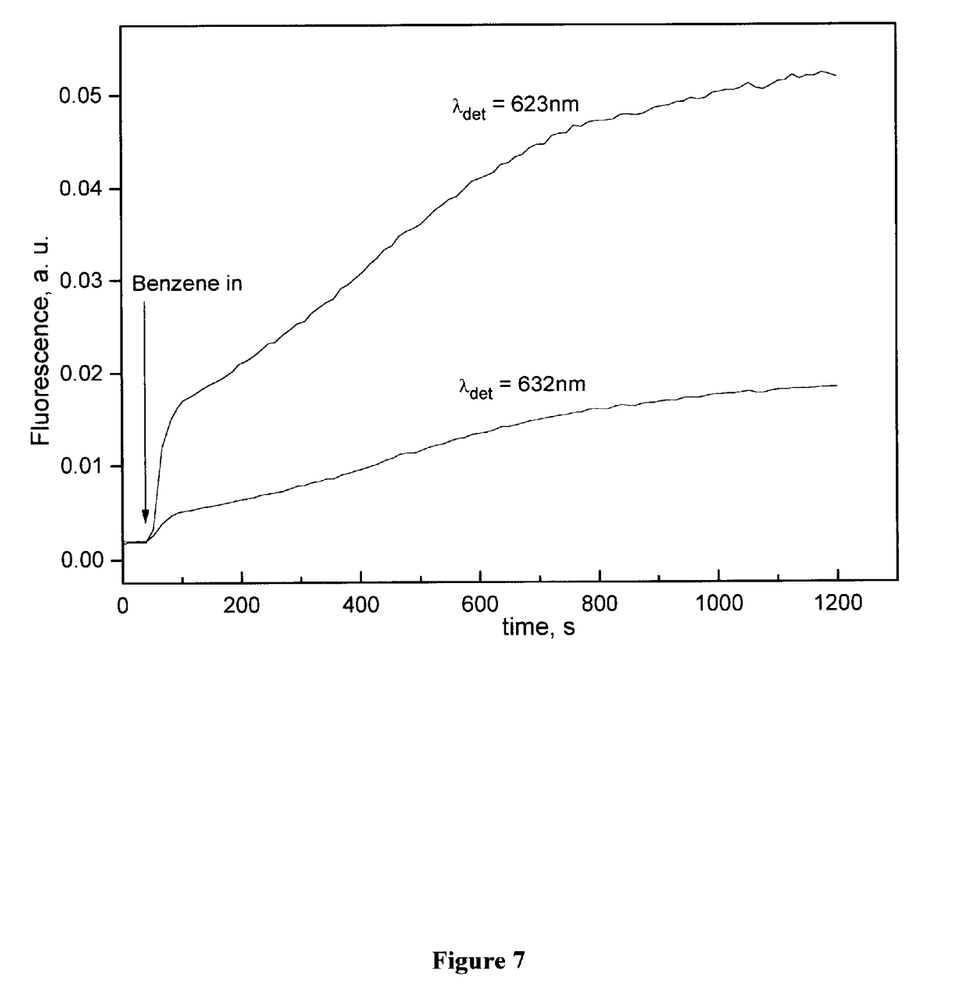
FIG. 7 shows time scan of Zn-TPP aggregate film under benzene exposure for two detecting wavelengths.

In another additional embodiment the sensitivity for particular Zn-TPP/vapor combinations can be improved by selecting detection wavelengths that are optimal for the particular system. For most analyte vapors the appearance of strong fluorescence band at 623 indicates that performance may be improved by choosing this wavelength for signal detecting. Time scan of the fluorescent response under benzene exposure using this wavelength (623 nm) is compared with that at non-optimal wavelength (632 nm) corresponding to the maximum of intensity prior exposure (FIG. 7). It is apparent that this improves the fluorescence response significantly. The same way for TPP aggregates, fluorescence detection at the optimal wavelength (650 nm, FIG. 3) can improve the sensitivity. Thus, the spectral shift and the redistribution of band intensities can provide effective amplification of the response signal.

In another preferred embodiment the proposed method of detection of organic vapors employs sensitive aggregated TPP and Zn-TPP compound incorporated into a waveguide or into a fiber-optic system having a flexible fiber-optic probe exhibiting enhanced sensitivity and improved reliability, yet low in cost. In one configuration, the fluorescent sensitive material is excited with a compact blue laser diode or LED generating, for example, at wavelength 405–430 nm.

In still another embodiment the light delivery and collection is performed using a U-bent fiber. It is known that due to sharp bending of the multimode fiber with radius of bending of about 1–2 mm the light escapes from the fiber core into its low-index cladding. After Fresnel reflection at the interface between the cladding and an external low-index media (or air), almost 80% of the light returns back into the fiber core. If the bent region of the fiber is coated with a sensitive fluorescent film, then the returned light will contain also some part of the fluorescent signal. In spite of very simple and cost-efficient design of such a fiber probe it does not provide maximum sensitivity. Length of the bent fiber region is relatively small resulting in a weak fluorescence response signal. Such fiber probe can be used in the applications that do not require very high sensitivity. In order to enhance the sensitivity one should increase the distance of light propagation in the fluorescence film. This is achieved, for example, by removing fiber cladding in the U-bent region (polishing it down to the fiber core) and depositing the fluorescent sensitive material directly on the fiber core.

Figure 8:
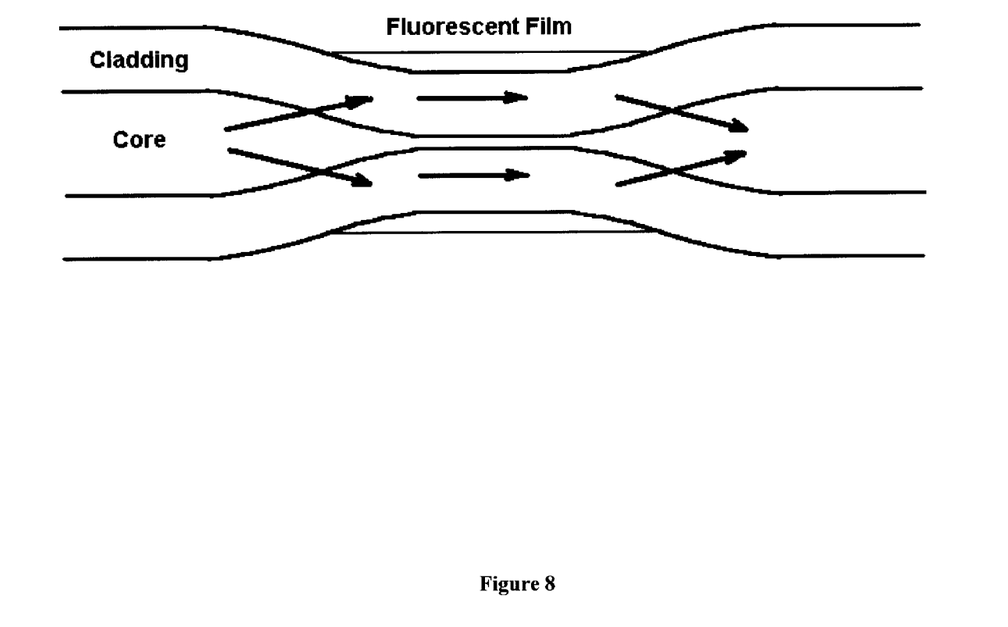
FIG. 8 Shows double tapered fiber probe.

In another preferred embodiment shown in FIG. 8 the light propagation distance of the fluorescent material is increased by employing a double tapered fiber configuration. It is known that as the fiber diameter decreases the light escapes from the fiber core and propagates in its cladding. The cladding coated with or made from thin fluorescent film guides the light due to total internal reflection at the cladding-air interface. At the second taper, where the fiber diameter increases, the light containing also the fluorescence signal re-couples back into the fiber core. Magnitude of the fluorescence signal extracted form the sensitive film by evanescent modes is proportional to the distance of light propagation through the polymer film. In the case of a double taper configuration the distance can be made as large as ten centimeters providing very high sensitivity. Removing of the fiber cladding and depositing the sensitive fluorescent material directly onto the fiber core allows further increasing the system sensitivity.

In additional preferred embodiment the sensitive fluorescent material is directly incorporated into the fiber-optic system playing a role of an optical waveguide. In that case the system sensitivity is enhanced by forcing the light to propagate through the sensitive material.

Thus, this method provides an efficient fluorescence-based means for highly sensitive and selective detection of organic vapors. As a general technology, the proposed method can find many useful applications for detecting different volatile organic compounds, such as vapors of benzene, alcohol, chloroform, dimethyl methylphosphonate (DMMP) that is a simulant of Sarin, Soman and other chemical warfare agents as required for environmental monitoring, chemical industry and medicine.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A method of detecting organic vapors employing at least one fluorescent sensitive material, comprising the steps of:

excitation of said at least one fluorescent sensitive material with at least one light source generating at the wavelengths required for efficient stimulating the fluorescence of said sensitive material, collecting the fluorescent light signal from said fluorescent sensitive material with a light collecting system, exposing the fluorescent sensitive material to the organic vapor, measuring spectrum of the fluorescence light signal after such exposure, processing the spectrum of the fluorescence light signal and comparing this spectrum with the spectrum obtained from the fluorescent sensitive material in the absence of the organic vapor, wherein said at least one fluorescent sensitive material comprises a thin film of self-quenching molecular aggregates of porhyrins, with said aggregates dissociating in the presence of the organic vapors, which leads to their enhanced fluorescence.

2. A method of detecting organic vapors of claim 1, wherein said sensitive fluorescent material is a thin film of tetraphenylporphyrin (TPP) or Zn-tetraphenylporphyrin (Zn-TPP) aggregates used for sorption of volatile organic compounds, such as vapors of benzene, alcohol, chloroform, dimethyl methylphosphonate (DMMP), Sarin, Soman and other chemical warfare agents.

3. A method of detecting organic vapors of claim 1, wherein said at least one fluorescent sensitive material is incorporated into a waveguiding system delivering light from said at least one light source and effectively collecting the signal light from said fluorescent sensitive material.

4. A method of detecting organic vapors of claim 3, wherein at least one section of said waveguiding system is made from said fluorescent sensitive material operating as a waveguide at wavelengths of said excitation light and said fluorescent signal light.

5. A method of detecting organic vapors of claim 3, wherein said waveguiding system incorporates at least one optical fiber having at least one sharp U-bend, and said fluorescent sensitive material having refractive index not less than the refractive index of the medium, in which molecules of the basis gas under detection are present, is deposited on outer surface of the fiber in the region of its said U-bend.

6. A method of detecting organic vapors of claim 5, wherein cladding of said fiber in said outer region of U-bend is removed before depositing said fluorescent sensitive material, thus improving excitation of the fluorescent sensitive materials and collecting of the fluorescent signal light.

7. A method of detecting organic vapors of claim 3, wherein said waveguiding system incorporates at least one optical fiber having at least one section with double tapered geometry characterized by decreasing and then increasing fiber diameter, and said fluorescent sensitive material, having refractive index not less than the refractive index of the medium in which molecules of the organic gas under detection are presents, is deposited on the surface of said fiber in its said double tapered region.

8. A method of detecting organic vapors of claim 7, wherein cladding of said fiber in said double tapered region is removed before depositing said fluorescent sensitive material, thus improving excitation of the fluorescent sensitive materials and collecting the fluorescent signal light.

* * * * *